(12) United States Patent
Yamamoto et al.

(10) Patent No.: US 8,408,400 B2
(45) Date of Patent: Apr. 2, 2013

(54) LIMPNESS DETECTING DEVICE, LIMPNESS DETECTING METHOD, AND SHEET HANDLING APPARATUS INCLUDING LIMPNESS DETECTING DEVICE

(75) Inventors: Takahiro Yamamoto, Tokyo (JP); Shota Kure, Kanagawa-ken (JP); Junji Miura, Kanagawa-ken (JP); Kazuhiro Itsumi, Tokyo (JP); Takeo Miki, Tokyo (JP); Seiji Ikari, Kanagawa-ken (JP); Kenji Miyazaki, Tokyo (JP); Takanobu Nishimura, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 155 days.

(21) Appl. No.: 12/943,309

(22) Filed: Nov. 10, 2010

(65) Prior Publication Data

US 2011/0108469 A1    May 12, 2011

(30) Foreign Application Priority Data

Nov. 12, 2009    (JP) .................................. 2009-259218

(51) Int. Cl.
*B07C 5/34*    (2006.01)
(52) U.S. Cl. .......................... 209/599; 209/576; 209/699
(58) Field of Classification Search .................... 73/159, 73/587, 852, 849; 209/571, 576, 582, 599, 209/699
See application file for complete search history.

(56) References Cited

U.S. PATENT DOCUMENTS

| | | | | |
|---|---|---|---|---|
| 4,365,508 | A | * 12/1982 | Loftus | ............................... 73/159 |
| 4,381,447 | A | * 4/1983 | Horvath et al. | ............ 250/223 R |
| 5,477,059 | A | * 12/1995 | Arakawa | ........................ 250/587 |
| 5,765,094 | A | * 6/1998 | Nakamura | ..................... 399/406 |

(Continued)

FOREIGN PATENT DOCUMENTS

| CN | 101490542 A | 7/2009 |
|---|---|---|
| CN | 101568831 A | 10/2009 |

(Continued)

OTHER PUBLICATIONS

Chinese Office Action dated Aug. 10, 2012.

(Continued)

*Primary Examiner* — Terrell Matthews
(74) *Attorney, Agent, or Firm* — Pillsbury Winthrop Shaw Pittman, LLP

(57)    ABSTRACT

According to one embodiment, a limpness detecting device includes a transmitting unit to irradiate an acoustic wave towards a conveyed sheet to excite a Lamb wave, a first receiving unit to detect a leaky wave of the Lamb wave emitted from a front surface of the sheet, a second receiving unit to detect a leaky wave of the Lamb wave emitted from a back surface of the sheet, a comparison data calculating unit to calculate comparison data based on the signal detected by the first receiving unit and the signal detected by the second receiving unit, and an intactness judgment unit to compare the comparison data calculated by the comparison data calculating unit with a preset standard value and judge whether the sheet is an intact bill or not, based on a result of the comparison.

14 Claims, 10 Drawing Sheets

U.S. PATENT DOCUMENTS

| | | | |
|---|---|---|---|
| 5,814,730 A | | 9/1998 | Brodeur et al. |
| 5,922,959 A | * | 7/1999 | Kayani .......................... 73/597 |
| 6,057,927 A | * | 5/2000 | Levesque et al. ............ 356/432 |
| 6,438,350 B1 | * | 8/2002 | Hasegawa et al. ............ 399/374 |
| 6,543,288 B1 | * | 4/2003 | Blouin et al. .................. 73/643 |
| 6,546,351 B1 | * | 4/2003 | Haycock et al. .............. 702/127 |
| 6,574,569 B1 | * | 6/2003 | Omata et al. .................... 702/33 |
| 7,191,657 B2 | * | 3/2007 | Maier et al. ..................... 73/587 |
| 8,156,808 B2 | * | 4/2012 | Itsumi et al. ................... 73/573 |
| 2007/0006654 A1 | | 1/2007 | Pradel |
| 2008/0302188 A1 | | 12/2008 | Yabushita et al. |
| 2009/0223295 A1 | | 9/2009 | Kondo |
| 2009/0293424 A1 | * | 12/2009 | Mori ............................... 53/167 |
| 2009/0312957 A1 | | 12/2009 | Domke et al. |

FOREIGN PATENT DOCUMENTS

| | | |
|---|---|---|
| DE | 10 2006 033 001 | 1/2008 |
| JP | 05-80605 | 11/1993 |
| JP | 2001-351141 | 12/2001 |
| JP | 2008-164394 | 7/2008 |
| JP | 2008-207885 | 9/2008 |
| WO | WO 2004/095380 | 11/2004 |
| WO | WO 2008/130111 | 10/2008 |

OTHER PUBLICATIONS

European Search Report dated Aug. 27, 2012.

* cited by examiner

US 8,408,400 B2

LIMPNESS DETECTING DEVICE, LIMPNESS DETECTING METHOD, AND SHEET HANDLING APPARATUS INCLUDING LIMPNESS DETECTING DEVICE

CROSS-REFERENCE TO RELATED APPLICATION

This application is based upon and claims the benefit of priority from Japanese Patent Application No. 2009-259218, filed on Nov. 12, 2009, the entire contents of which are incorporated herein by reference.

FIELD

Exemplary embodiments herein related to a limpness detecting device for detecting limpness of a sheet, a limpness detecting method, and a sheet handling apparatus including a limpness detecting device.

BACKGROUND

Conventionally, sheet handling apparatuses have been put into practice that count and discriminate various types of sheets. A sheet handling apparatus takes in sheets inserted into an insert port one by one, and conveys the sheets to an inspection device. The inspection device subjects the sheet to various sorts of processing and discriminates the state of the sheet. For example, if the sheet is a banknote, the sheet handling apparatus may carry out a judgment on the type of the sheet, a judgment on whether the banknote is genuine or false, and a judgment on whether the sheet is fit for recirculation (intactness judgment), based on the inspection result of the inspection device.

The sheet handling apparatus judges that sheets with deteriorated rigidity are not fit for recirculation. For this reason, the inspection device detects such mechanical properties as how much the rigidity of the sheet has deteriorated.

For example, Japanese Patent Publication No. H5-80605 discloses a technology in which an acoustic wave is irradiated towards a sheet, and the weight per unit area of the sheet is measured based on the level of the reflecting wave and the transmitted wave.

Japanese Laid-Open Patent Publication No. 2008-164394 discloses a technology in which an ultrasonic wave is irradiated onto a test object, such as a metal plate, leaky waves of the waves propagated by the test object are received, and defects in the test object are detected based on the amplitude of the received waveform.

However, there are cases in which the sheets that are inspected by apparatuses including the above-described technologies have ink or the like printed on their surface. In this case, there is the possibility that the ink adhering to the surface of the sheet influences the irradiation and emission properties of acoustic waves with respect to the medium as well as the waves propagating through the medium.

The designs printed on the sheet may differ between the front surface and the back surface. Therefore, also the inspection result may differ depending on whether the front surface or the back surface opposes the inspection device. Furthermore, the inspection result may also differ depending on the conveying orientation of the conveyed sheets.

Depending on the front surface and the back surface, there are variations in the conveying state of the sheets that are conveyed to the inspection device. Moreover, there are variations in the conveying orientation of the sheets that are conveyed to the inspection device. As a result, there is the problem that the inspection device may not be able to judge accurately the intactness of the sheet.

Furthermore, there may be folding lines or the like in the sheet, and there is the problem that such a folding line in the sheet may influence the waves leaking from the front surface or back surface of the sheet (leaky waves).

DETAILED DESCRIPTION

In general, according to one embodiment, there is provided a limpness detecting device including: a transmitting unit for irradiating an acoustic wave towards a conveyed sheet to excite a Lamb wave; a first receiving unit for detecting a leaky wave of the Lamb wave emitted from a front surface of the sheet; a second receiving unit for detecting a leaky wave of the Lamb wave emitted from a back surface of the sheet; a comparison data calculating unit for calculating comparison data based on the signal detected by the first receiving unit and the signal detected by the second receiving unit; and an intactness judgment unit for comparing the comparison data calculated by the comparison data calculating unit with a preset standard value and judging whether the sheet is an intact bill or not, based on a result of the comparison.

Referring to the accompanying drawings, the following is a detailed explanation of a limpness detecting device, a limpness detecting method and a sheet handling apparatus including a limpness detecting device in accordance with one embodiment of the present invention.

Figure 1:
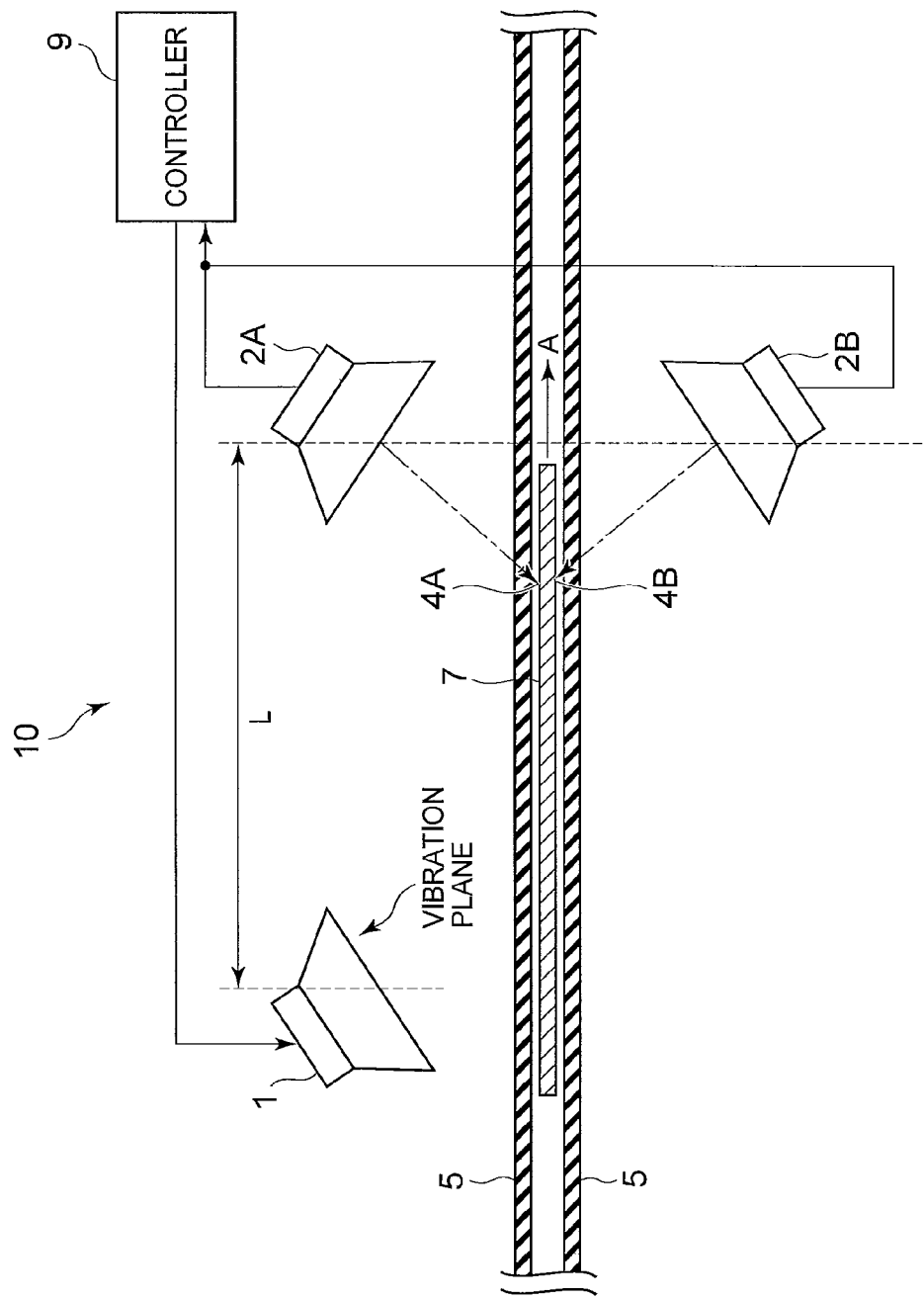
FIG. 1 is a diagrammatic view showing a configuration example of a limpness detecting device according to one embodiment.

FIG. 1 is an illustrative drawing showing a configuration example of a limpness detecting device according to one embodiment. The limpness detecting device 10 inspects the mechanical quality of a sheet 7. For example, the limpness detecting device 10 detects the limpness of a paper, which is defined for example as the modulus of elasticity, the tensile strength or the flexural strength of the sheet 7. The limpness detecting device 10 is arranged near a conveying portion of a sheet handling apparatus, for example.

As shown in FIG. 1, the limpness detecting device 10 includes a transmitter 1, receivers 2A and 2B, and a controller 9.

The transmitter 1 functions as a transmitting unit for exciting Lamb waves by irradiating acoustic waves towards the conveyed sheet 7. The transmitter 1 is a supersonic wave generator that excites Lamb waves (plate waves) in the sheet 7.

The transmitter 1 includes for example a speaker, a piezoelectric transducer or a vibration generator using a microelectromechanical system (MEMS). The transmitter 1 causes a vibrating surface to vibrate in accordance with an applied voltage, thus generating acoustic waves. The transmitter 1 is arranged on the upstream side with respect to the receiver 2A and the receiver 2B.

The receiver 2A and the receiver 2B are receivers that detect the Lamb waves generated in the sheet 7. The receiver 2A and the receiver 2B function as receiving units for detecting leaky waves of the Lamb waves emitted from a detecting point on the front surface or the back surface of the sheet.

The receiver 2A and the receiver 2B have the same configuration as the transmitter 1, and include for example, a receiving sensor such as a microphone or a piezoelectric transducer, or a displacement meter (interferometer) that uses interference light to measure a vibration as a displacement. The receiver 2A and the receiver 2B obtain a voltage in accordance with a vibration of a vibration surface that is excited by a wave leaking from the sheet 7.

The transmitter 1 as well as the receiver 2A and the receiver 2B include a vibration surface. A vibration surface can be displaced in accordance with the applied voltage. Moreover, a vibration surface can generate a voltage in accordance with the displacement of the surface. That is to say, the transmitter 1 causes its vibration surface to vibrate by applying a voltage to the vibration surface, thus generating a wave.

Moreover, the receiver 2A and the receiver 2B detect a voltage that is generated by the displacement of their vibration surface, which is vibrated by the wave. It is assumed that the transmitter 1 emits an acoustic wave in a direction that is perpendicular to the vibration surface. Moreover, it is assumed that the receiver 2A and the receiver 2B detect an acoustic wave that is irradiated in a direction perpendicular to the vibration surface.

As shown in FIG. 1, the receiver 2A and the receiver 2B are provided at positions opposing each other. That is to say, the receiver 2A is provided on the same side as the transmitter 1. Moreover, the receiver 2B is provided at a position opposing the receiver 2A. The transmitter 1 is separated from the receiver 2A and the receiver 2B by a distance L in the conveying direction A of the sheet 7.

The transmitter 1 irradiates acoustic waves onto the conveyed sheet 7. Moreover, the receiver 2A and the receiver 2B detect leaky waves of the Lamb waves propagating through the conveyed sheet 7. However, if the acoustic waves are emitted towards the sheet 7 in a non-contacting manner, then the attenuation of the acoustic waves is large. Therefore, the transmitter 1, the receiver 2A and the receiver 2B are placed at positions close to the sheet 7 conveyed by conveying belts 5.

The conveying belts 5 function as a conveyer. As shown in FIG. 1, the conveying belts 5 are provided as a pair of upper and lower belts. The conveying belts 5 are driven by drive pulleys or the like. The conveying belts 5 sandwich the sheet 7 between the pair of upper and lower belts and convey it at a constant speed in the conveying direction A shown in FIG. 1.

A controller 9 carries out the overall control of the limpness detecting device 10. The controller 9 includes, for example, a CPU, a buffer memory, a program memory and a non-volatile memory. The CPU carries out various kinds of arithmetic processing. The buffer memory temporarily stores the results computed by the CPU. The program memory and the non-volatile memory store various kinds of programs executed by the CPU as well as control data. The controller 9 can perform various kinds of processes by executing a program stored in the program memory with the CPU. For example, the controller 9 controls the operation timing of the transmitter 1, the receiver 2A and the receiver 2B. In the present embodiment, the controller 9 performs the control such that waves are detected simultaneously by the receiver 2A and the receiver 2B.

Moreover, the controller 9 includes a signal processing unit for processing signals that are detected by the receiver 2A and the receiver 2B, and an intactness judgment unit for judging intactness. The signal processing unit and the intactness judgment unit are discussed in detail further below.

When the limpness detecting device 10 detects a sheet 7, it generates supersonic waves with the transmitter 1. Thus, the limpness detecting device 10 irradiates supersonic waves onto the sheet 7. In the sheet 7, Lamb waves are excited by these supersonic waves. The excited Lamb waves generate leaky waves from the front surface and the back surface of the sheet 7, while being propagated inside the sheet 7. The limpness detecting device 10 detects the leaky waves of the Lamb waves with the receiver 2A and the receiver 2B.

Lamb waves are waves that are propagated inside thin plates while causing a flexing or contracting/expanding motion along the thin plates. The diffusive decay of Lamb waves is proportional to the square root of the propagation distance, and the distribution of displacement and stress is substantially constant across the entire plate cross-section and is not affected by local changes in the material constants, so that the propagation behavior is determined by the mechanical properties of the overall plate.

The sheet 7 is made of fibers and binder. However, if the sheet 7 is subject to bill fatigue, binder is lost and the relative content of air increases. As a result, the sheet 7 subject to bill fatigue has a lower density than a bill not subject to bill fatigue. When the proportion of air in the sheet 7 becomes large, the physical quality of the sheet 7 becomes closer to the physical quality of air. Therefore, the acoustic resistance drops. That is to say, before propagating through the sheet 7, the Lamb waves disperse to the outside. As a result, the Lamb waves attenuate before they reach the detecting points 4A and 4B of the receiver 2A and the receiver 2B, and the amplitude of the waves detected by the receiver 2A and the receiver 2B decreases.

As noted above, the controller 9 of the limpness detecting device 10 according to the present embodiment judges, based on the level (amplitude) of a signal detected by the receiver 2A and the receiver 2B, whether the sheet 7 is an intact bill or a damaged bill. Therefore, the controller 9 includes a standard value memory 15, which stores a standard value serving as a reference for the judgment as described further below.

Figure 2:
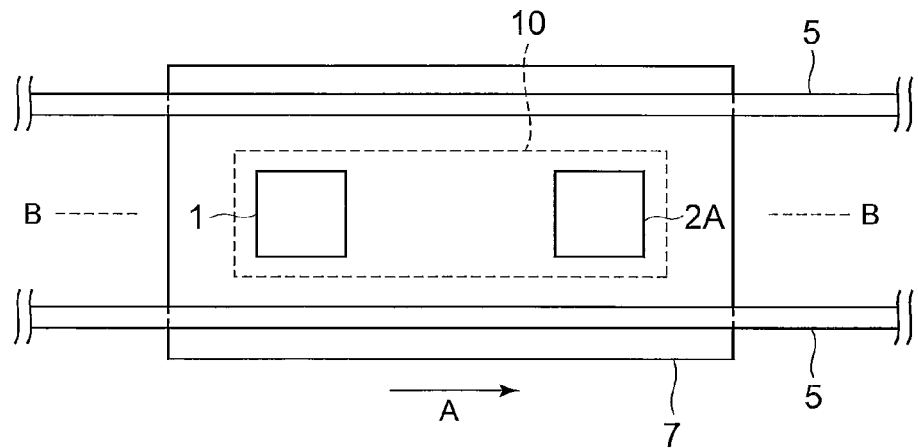
FIG. 2 is a plan view illustrating the operation of the limpness detecting device shown in FIG. 1.

FIG. 2 is a view showing the limpness detecting device 10 shown in FIG. 1 as viewed from the side of the transmitter 1. As shown in FIG. 2, the limpness detecting device 10 includes the transmitter 1 and the receiver 2A, which are placed one behind the other in the conveying direction of the sheet 7. Moreover, the limpness detecting device 10 includes a receiver 2B (not shown in FIG. 2), which is positioned on the other side of the sheet 7, such that the sheet 7 is arranged between the receiver 2A and the receiver 2B. It should be noted that the receiver 2A and the receiver 2B are arranged such that they always detect leaky waves from the same region (detecting points 4A and 4B) on the conveyed sheet 7. That is to say, the receiver 2A and the receiver 2B are arranged at a position where the centers of the vibration surfaces of the receiver 2A and the receiver 2B overlap the center in width direction of the conveyed sheet 7.

Figure 3:
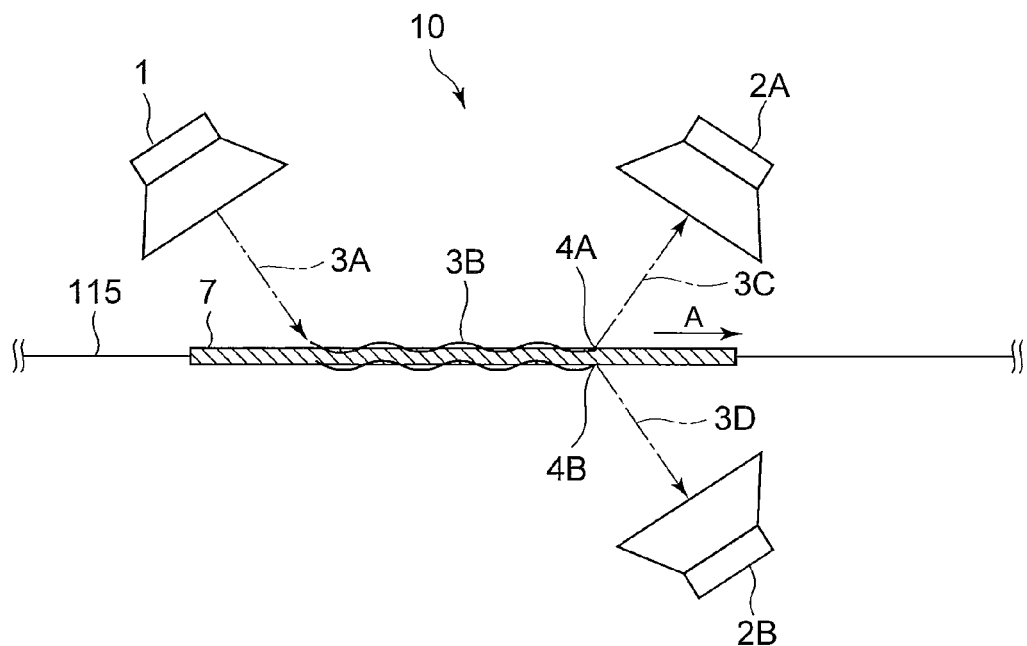
FIG. 3 is a diagrammatic view showing the arrangement of the various parts of the limpness detecting device.

FIG. 3 is a cross-sectional view in which the limpness detecting device 10 shown in FIG. 2 is cut along the line B-B. The transmitter 1 emits acoustic waves 3A from its vibration surface, and Lamb waves 3B are excited within the sheet 7 that is conveyed along a conveying route 115. The Lamb waves 3B are propagated within the sheet 7.

The Lamb waves 3B propagated by the sheet 7 cause emission of leaky waves 3C from the detecting point 4A of the receiver 2A on the sheet 7. Moreover, the Lamb waves 3B cause emission of leaky waves 3D from the detecting point 4B of the receiver 2B on the sheet 7. The receiver 2A generates a voltage based on the leaky waves 3C, and outputs this voltage to the controller 9. The receiver 2B generates a voltage based on the leaky waves 3D, and outputs this voltage to the controller 9.

It should be noted that the limpness detecting device 10 can be arranged to be compact by making the distance in horizontal direction between the point of incidence where the acoustic waves emitted from the transmitter 1 are incident and the detecting points 4A and 4B of the receiver 2A and the receiver 2B as small as possible, within a range in which the receiver 2A and the receiver 2B can receive the Lamb waves and a sufficiently high S/N ratio can be maintained.

Figure 4:
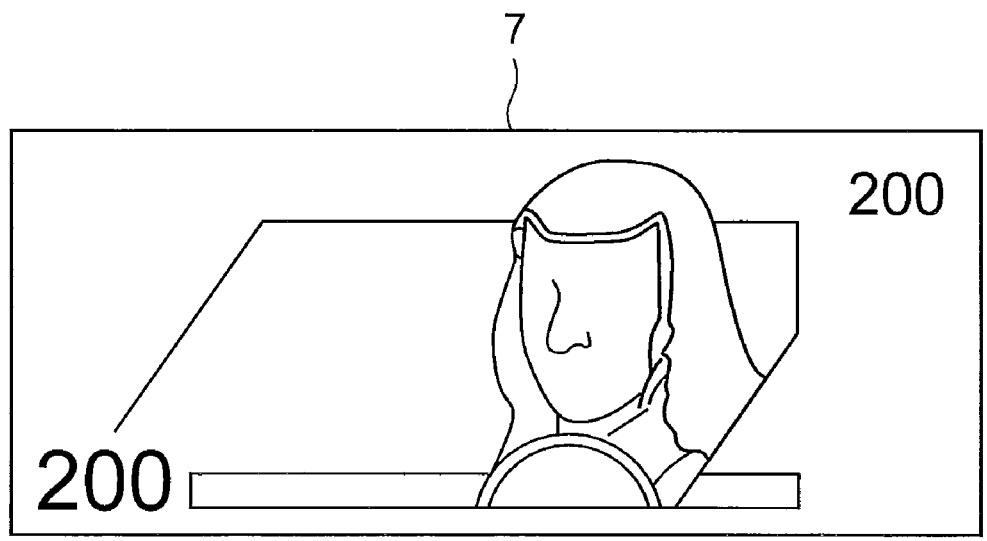
FIG. 4 is a diagram showing a sheet that is inspected by the limpness detecting device.
Figure 5:
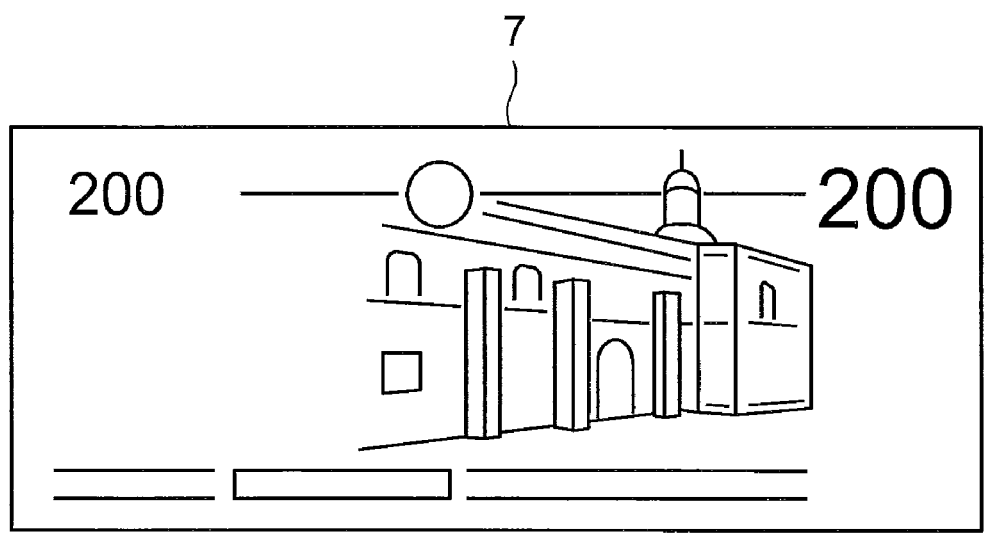
FIG. 5 is a diagram showing a sheet that is inspected by the limpness detecting device.

FIGS. 4 and 5 are views illustrating an example of the sheet 7 that is inspected by the limpness detecting device 10 according to the present embodiment. FIG. 4 is a view showing an example of a front surface of the sheet 7. FIG. 5 is a view showing an example of a back surface of the sheet 7. Moreover, FIG. 6 is a diagrammatic view illustrating the amount of ink that is applied to the sheet 7.

As shown in FIG. 4 and FIG. 5, the print pattern differs between the front surface and the back surface. Therefore, as shown in FIG. 6, also the amount of ink 8 that is applied to the sheet 7 differs between the front surface and the back surface. In the example shown in FIG. 6, there is more ink 8 applied to the front surface than to the back surface.

Figure 6:
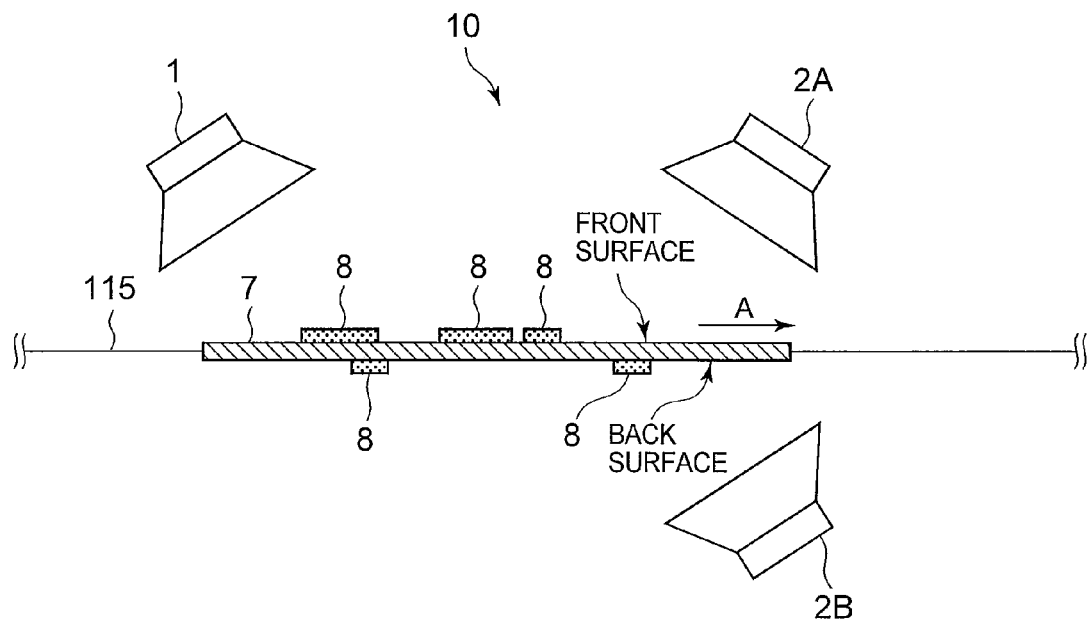
FIG. 6 is a diagrammatic view illustrating an example in which the sheet is inspected with the limpness detecting device.
Figure 7:
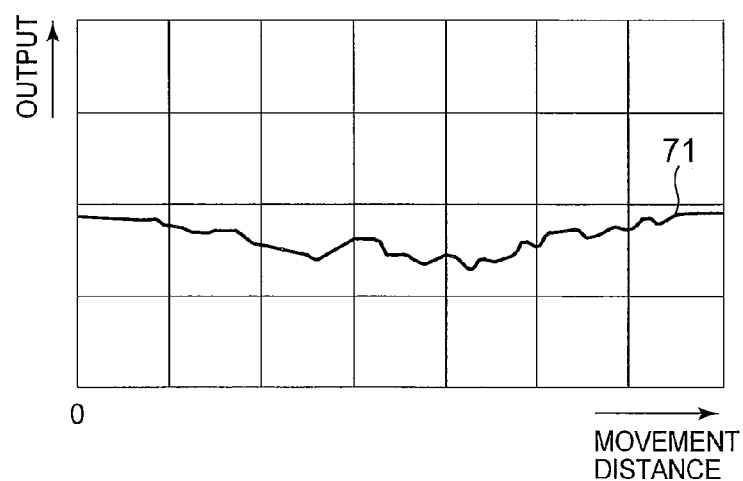
FIG. 7 is a graph showing a waveform of the sheet that is detected by a receiver of the limpness detecting device.
Figure 8:
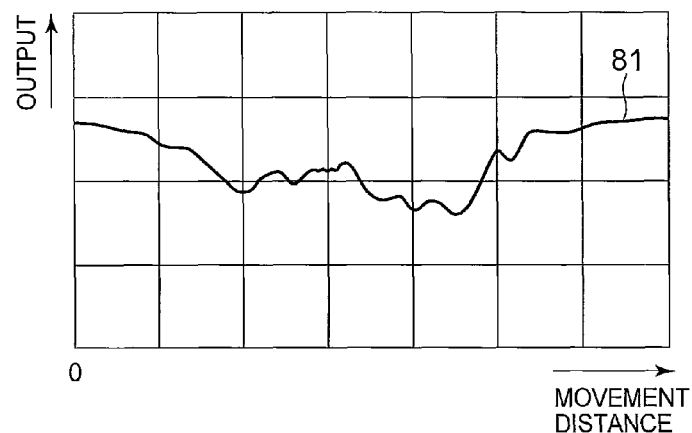
FIG. 8 is a graph showing a waveform of the sheet that is detected by a receiver of the limpness detecting device.

FIG. 7 is a graph illustrating a signal that is detected by the receiver 2A in the example shown in FIG. 6. That is to say, the signal 71 shown in FIG. 7 is a signal of the detection of the leaky waves that are leaked from the front surface, where there is a greater amount of ink 8. Moreover, FIG. 8 is a graph illustrating a signal that is detected by the receiver 2B in the example shown in FIG. 6. That is to say, the signal 81 shown in FIG. 8 is a signal of the detection of the leaky waves that are leaked from the back surface, where there is a smaller amount of ink 8.

It should be noted that the signals 71 and 81 shown in FIG. 7 and FIG. 8 show the crest values of the leaky waves continuously detected from the conveyed sheet 7. The horizontal axis of the signal shown in FIG. 7 and FIG. 8 denotes the movement distance of the detecting points 4A and 4B of the receiver 2A and the receiver 2B on the sheet 7, taking the front end of the sheet 7 as zero. Moreover, the vertical axis of the signal shown in FIG. 7 and FIG. 8 denotes a value corresponding to the crest value of the leaky waves detected by the receiver 2A and the receiver 2B.

The ink 8 acts as a foreign substance that impedes the leaking of Lamb waves propagating through the sheet 7 out of the sheet 7. If the limpness of the sheet 7 is detected using Lamb waves, the detection result of the receiver 2A and the receiver 2B is affected by the amount of ink 8 that is applied to the sheet 7. Therefore, as shown in FIGS. 7 and 8, the leaky waves leaking from the front surface where the amount of ink 8 is large have crest values that are smaller than the leaky waves leaking from the back surface where the amount of ink 8 is small. It should be noted that the signal of the leaky waves detected by the receiver 2A and the receiver 2B takes on a level whose crest values are smaller as the degree of bill fatigue becomes higher.

Figure 9:
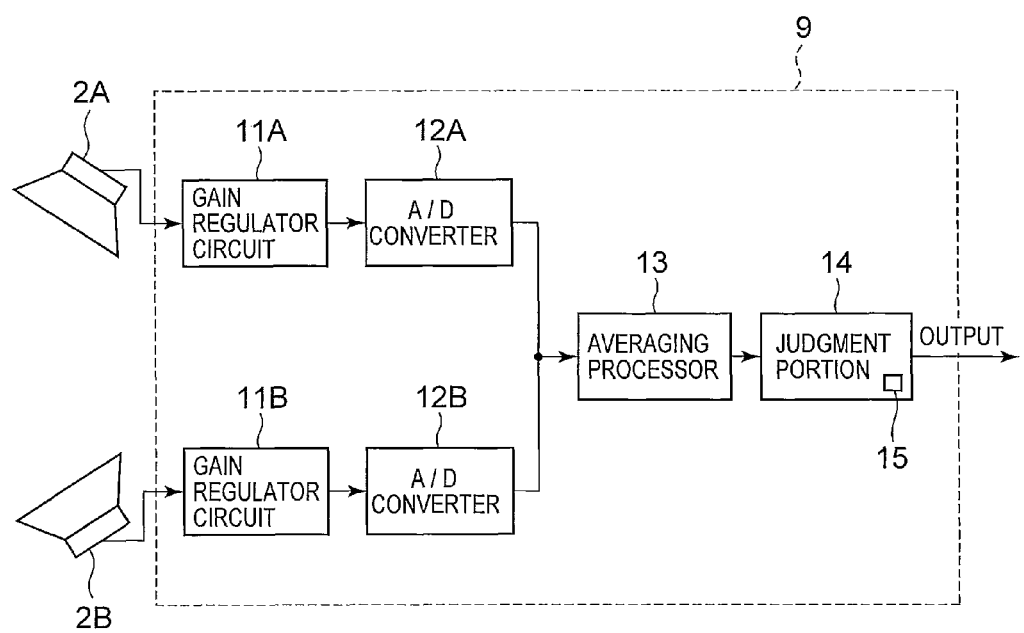
FIG. 9 is a block diagram showing the configuration of a signal processing system of the limpness detecting device.

FIG. 9 is a block diagram illustrating the controller 9 shown in FIG. 1. The controller 9 includes gain regulator circuits 11A and 11B, analog-digital converters 12A and 12B, an averaging processor 13, and a judgment portion 14.

The receiver 2A and the receiver 2B input the signal of the leaky waves detected from one entire sheet into the gain regulator circuits 11A and 11B. That is to say, the signals 71 and 81 of the leaky waves detected from the front surface and the back surface of one sheet are input into the gain regulator circuits 11A and 11B.

The gain regulator circuits 11A and 11B and the analog-digital converters (A/D converters) 12A and 12B function as signal processing units. It should be noted that the gain regulator circuits 11A and 11B function as gain regulating units. The gain regulator circuit 11A amplifies the signal that is output from the receiver 2A with a preset amplification ratio. The gain regulator circuit 11B amplifies the signal that is output from the receiver 2B with a preset amplification ratio. The gain regulator circuit 11A inputs the amplified signal into the A/D converter 12A. The gain regulator circuit 11B inputs the amplified signal into the A/D converter 12B.

It should be noted that the waves transmitted in the medium containing Lamb waves propagating through the sheet 7 have the characteristic that more waves leak to the side where the waves are incident. For this reason, the signal that is detected by the receiver 2A that is placed on the same side as the transmitter 1 will be larger than the signal that is detected by the receiver 2B, even if the sheet 7 is a uniform medium.

Accordingly, in this embodiment, the amplification ratio of the gain regulator circuit 11B is set to be larger than that of the gain regulator circuit 11A. For example, the controller 9 sets the amplification ratios of the gain regulator circuit 11A and the gain regulator circuit 11B such that the detection result for a uniform sheet 7 without printing takes on the same value for the receiver 2A and the receiver 2B.

The A/D converter 12A converts the analog signal that is input from the gain regulator circuit 11A into a digital signal. The A/D converter 12B converts the analog signal that is input from the gain regulator circuit 11B into a digital signal. The A/D converters 12 input the converted analog signals into an averaging processor 13. That is to say, the gain regulator circuits 11A and 11B and the A/D converters 12A and 12B subject the signal that is output from the receiver 2A and the signal that is output from the receiver 2B to signal processing, and output the signals to the averaging processor 13.

The averaging processor 13 and the judgment portion 14 function as an intactness judgment unit. The averaging processor 13 averages the signals that are input from the A/D converter 12A and the A/D converter 12B. That is to say, the averaging processor 13 averages the signal of the leaky waves leaking from the front surface of the sheet 7 and the signal of the leaky waves leaking from the back surface of the sheet 7.

Figure 10:
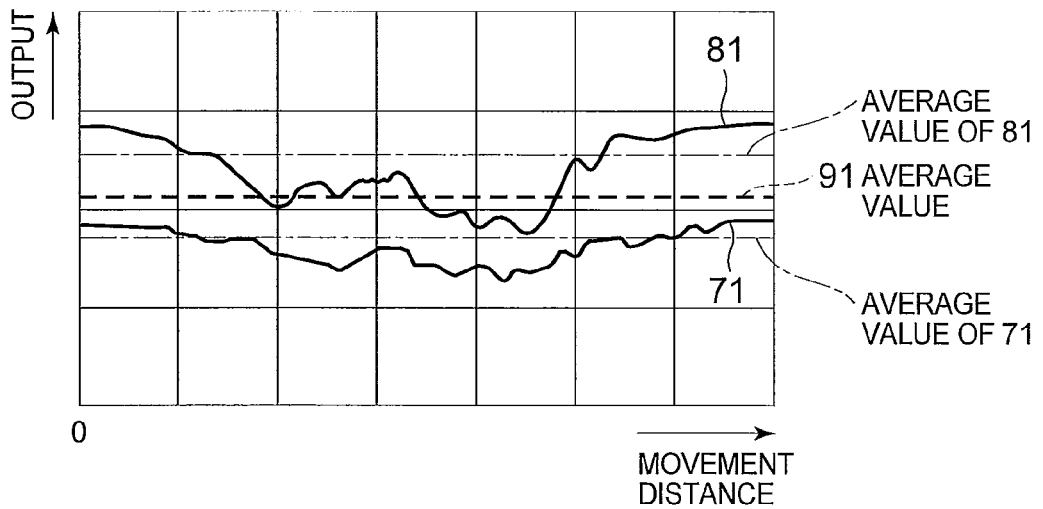
FIG. 10 is a graph showing a method for processing the signal waveform detected by the receiver of the limpness detecting device.

The averaging processor 13 functions as a unit for calculating comparative data that calculates comparative data based on the signal detected by the receivers 2A and 2B. As shown in FIG. 10, the averaging processor 13 calculates an average value 91 as comparative data, based on the signal 71 detected by the receiver 2A and the signal 81 detected by the receiver 2B. That is to say, the averaging processor 13 calculates the overall average value 91 of the signal 71 detected by the receiver 2A and the signal 81 detected by the receiver 2B. The averaging processor 13 inputs the calculated average value 91 into the judgment portion 14.

The judgment portion 14 includes the standard value memory 15, in which standard values are stored in advance. The standard value memory 15 stores a standard value serving as a reference for the judgment for each type of sheet 7.

The judgment portion 14 compares the standard value stored in the standard value memory 15 with the average value 91 that is input from the averaging processor 13, and judges whether the sheet 7 is an intact bill or not. The judgment portion 14 functions as an intactness judgment unit that compares the comparative data calculated by the averaging processor 13 with the preset standard value, and judges whether the sheet 7 is an intact bill, based on the comparison result.

That is to say, the judgment portion 14 judges that the sheet 7 is an intact bill if the average value 91 that is input from the averaging processor 13 is at least the standard value stored in the standard value memory 15. Moreover, the judgment portion 14 judges that the sheet 7 is a damaged bill if the average value 91 that is input from the averaging processor 13 is less than the standard value stored in the standard value memory 15.

It should be noted that the standard value memory 15 is configured to store the standard values in advance, but there is no limitation to this configuration. For example, a configuration is also possible in which sheets 7 are processed by the limpness detecting device 10, and then the standard value is set. In this case, the limpness detecting device 10 processes sheets 7 that have been judged in advance to be intact bills and sheets 7 that have been judged in advance to be damaged bills, and signals are detected from the respective sheets 7. The limpness detecting device 10 calculates standard values based on the detected signals values, and stores the calculated standard values in the standard value memory 15.

For example, the limpness detecting device 10 calculates an average value of the signal of the front surface and the signal of the back surface from the sheet 7 with the above-described method. The limpness detecting device 10 stores average values that are further averaged from the calculated average values of the damaged bills and of the intact bills as standard values in the standard value memory 15.

As noted above, the limpness detecting device 10 according to the present embodiment irradiates acoustic waves with the transmitter 1 onto the conveyed sheet 7. The limpness detecting device 10 detects leaky waves of the Lamb waves emanating from the front side and the rear side of the sheet 7 with the receiver 2A and the receiver 2B. The controller 9 of the limpness detecting device 10 calculates the average value 91 of the signal detected by the receiver 2A and the signal detected by the receiver 2B. The limpness detecting device 10 compares the calculated average value 91 with a standard value stored in advance and judges whether the sheet 7 is an intact bill. Thus, the limpness detecting device 10 can carry out an intactness judgment of the sheet 7, even if only the front side or only the rear side of the sheet 7 faces the transmitter 1.

As a result, a limpness detecting device, a limpness detecting method and a sheet handling apparatus provided with a limpness detecting device can be provided that can detect the limpness of the sheet with high accuracy.

It should be noted that in the present embodiment, a configuration has been explained in which the limpness detecting device 10 calculates an average value of the signal detected with the receiver 2A and the signal detected with the receiver 2B, and compares the calculated average value with a standard value, but there is no limitation to this configuration. For example, it is also possible that the limpness detecting device 10 calculates the sum of the signal detected with the receiver 2A and the signal detected with the receiver 2B, and compares the calculated value with a standard value. It should be noted that the standard value stored in the standard value memory 15 should be set as appropriate in accordance with the method of comparison. Moreover, the method of comparison may be any method that compares the value based on the signal detected by the receiver 2A and the signal detected by the receiver 2B with the standard value.

Moreover, the receivers 2 in the present embodiment have been explained to have a configuration in which leaky waves are detected from detecting points at a portion of the conveyed sheet 7, as shown in FIG. 2, but there is no limitation to this. A configuration in which the leaky waves from the entire sheet 7 are detected by arranging a plurality of receivers 2 is possible as well.

Figure 11:
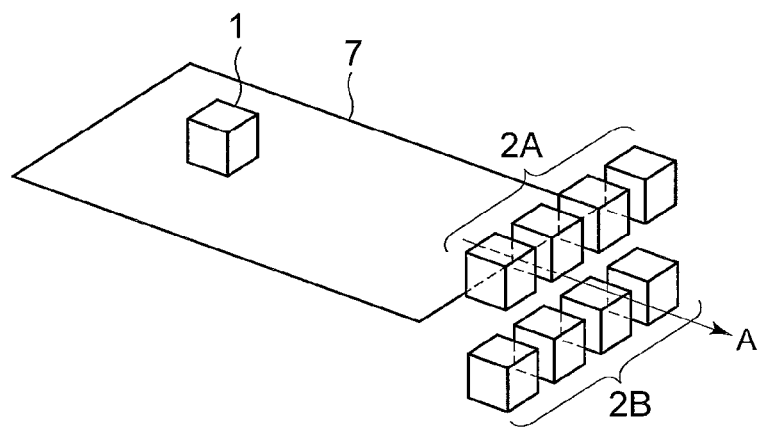
FIG. 11 is a diagrammatic perspective view showing another configuration example of the receivers of the limpness detecting device.

FIG. 11 is a perspective view showing another configuration example of the receivers 2 of the limpness detecting device 10. As shown in FIG. 11, the receiver 2A and the receiver 2B include a plurality of transducers that are lined up in a row at a right angle to the conveying direction of the sheet 7. These transducers are placed over a width that covers at least the region through which the sheet 7 is conveyed. Thus, the receiver 2A and the receiver 2B can detect the leaky waves from the entire sheet 7.

It should be noted that in this case, the averaging processor 13 calculates the average value 91 by averaging the level of the signals detected by the transducers.

Moreover, the transducers of the receiver 2A and the receiver 2B can be configured to have any shape. Therefore, it is also possible to provide a configuration in which the leaky waves from the entire sheet 7 are detected by modifying the shape of the transducers of the receiver 2A and the receiver 2B.

Figure 12:
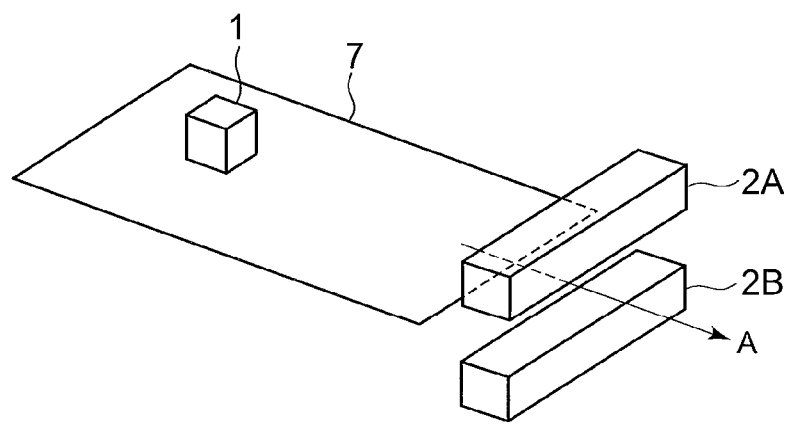
FIG. 12 is a diagrammatic perspective view showing another configuration example of the receivers of the limpness detecting device.

FIG. 12 is a perspective view showing another configuration example of the receivers 2 of the limpness detecting device 10. As shown in FIG. 12, the receiver 2A and the receiver 2B are placed over a width that covers at least the region through which the sheet 7 is conveyed in a direction perpendicular to the conveying direction of the sheet 7. That is to say, the vibration surfaces of the receiver 2A and the receiver 2B have a length of at least the width of the sheet 7. By placing such transducers, the receiver 2A and the receiver 2B can detect the leaky waves from the entire sheet 7.

Figure 13:
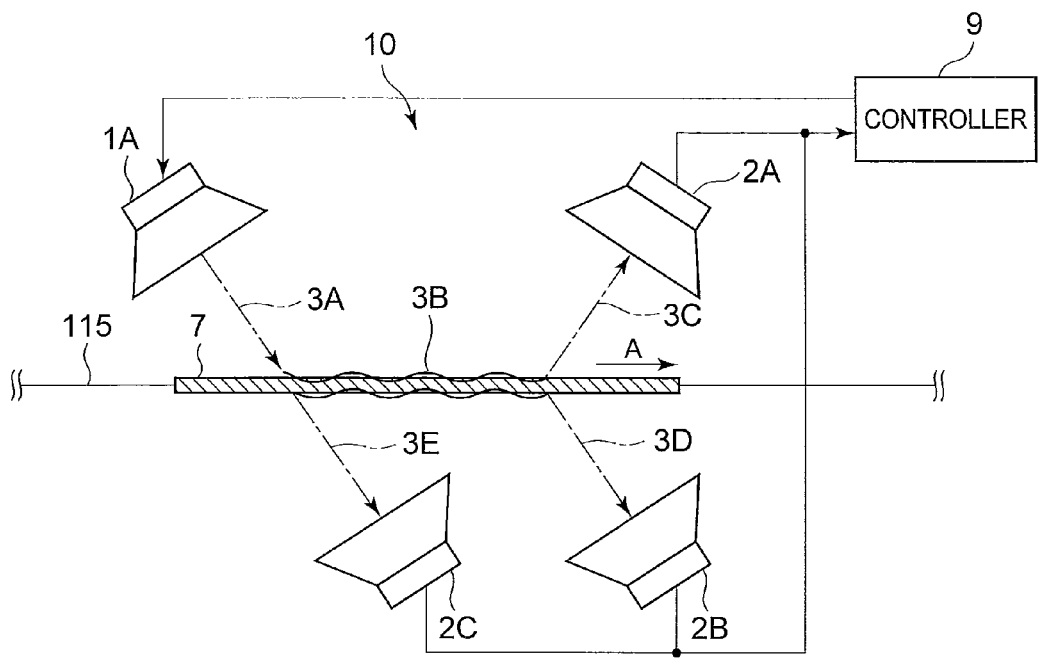
FIG. 13 is a diagrammatic view showing another configuration example of the receivers of the limpness detecting device.

Moreover, the limpness detecting device 10 also may have a configuration in which it is further provided with a receiver 2C. FIG. 13 is a diagram illustrating another configuration example of the receivers 2 of the limpness detecting device 10. The limpness detecting device 10 shown in FIG. 13 includes furthermore a receiver 2C in addition to the configuration shown in FIG. 3.

The receiver 2C has the same configuration as the receivers 2A and 2B, and is placed at a position opposing the transmitter 1, on the other side of the sheet 7. That is to say, the vibration surface of the receiver 2C is placed at the same angle as the vibration surface of the transmitter 1. Moreover, the receiver 2C is placed such that the center of the vibration surface of the receiver 2C overlaps with a line extending from the center of the vibration surface of the transmitter 1 in a direction perpendicular to the vibration surface of the transmitter 1.

Some of the waves emitted from the transmitter 1 and irradiated onto the sheet 7 percolate to the opposite side of the transmitter 1. The receiver 2C detects the percolation waves 3E percolating through the sheet 7. The percolation waves 3E percolating through the sheet 7 are affected by the state of the sheet 7. Based on the signal detected by the receiver 2C, the controller 9 detects that a plurality of sheets 7 are overlapping, or that a foreign substance such as a tape is attached to the sheet 7. In this case, the controller 9 functions as a foreign substance detecting unit.

Figure 14:
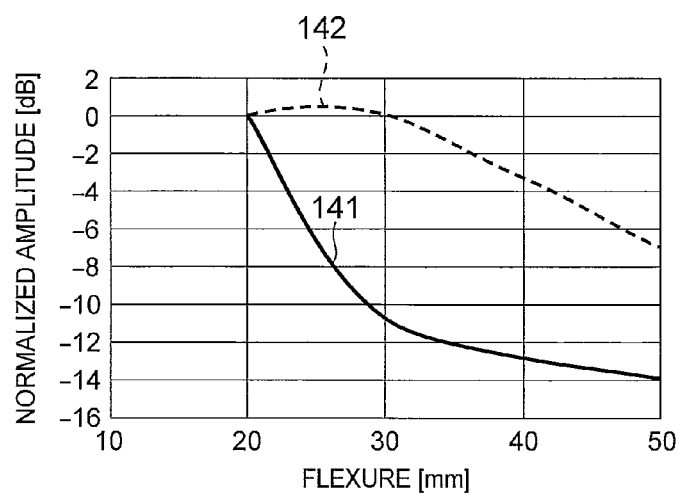
FIG. 14 is a graph illustrating the relation between the intensity of the percolation waves and the waves transmitted through the medium as well as the degree of bill fatigue.

Moreover, the percolation waves are also affected if the degree of bill fatigue of the sheet 7 is high. FIG. 14 is a graph illustrating the relation between the degree of bill fatigue of the sheet 7 and the leaky waves of the percolation waves and the Lamb waves. The horizontal axis indicates a value (flexure [mm]) quantifying the degree of bill fatigue of the sheet 7. The vertical axis denotes an amplitude (normalized amplitude [dB]) of the waves detected by the receiver 2A, the receiver 2B and the receiver 2C.

The curve line 141 indicates an average value of the amplitude of the wave detected by the receiver 2A and the amplitude of the wave detected by the receiver 2B. Moreover, the curve line 142 denotes the amplitude of the percolation wave detected by the receiver 2C.

As shown in FIG. 14, if for example the degree of bill fatigue of the sheet 7 is low (fore example, Flexure=20), then the curve line 141 and the curve line 142 indicate a high amplitude. And if for example the degree of bill fatigue of the sheet 7 is intermediate (for example, Flexure=30), then the curve line 141 indicates a small amplitude and the curve line 142 indicates a large amplitude. And if the degree of bill fatigue of the sheet 7 is high (for example, Flexure=50), then the curve line 141 and the curve line 142 both indicate a low amplitude.

As noted above, the change with respect to the degree of bill fatigue of the sheet 7 is larger for the Lamb waves than for the percolation waves. Accordingly, by setting for example individual threshold values for the Lamb waves and the percolation waves, the degree of bill fatigue of the sheet 7 can be detected in a stepwise manner.

Figure 15:
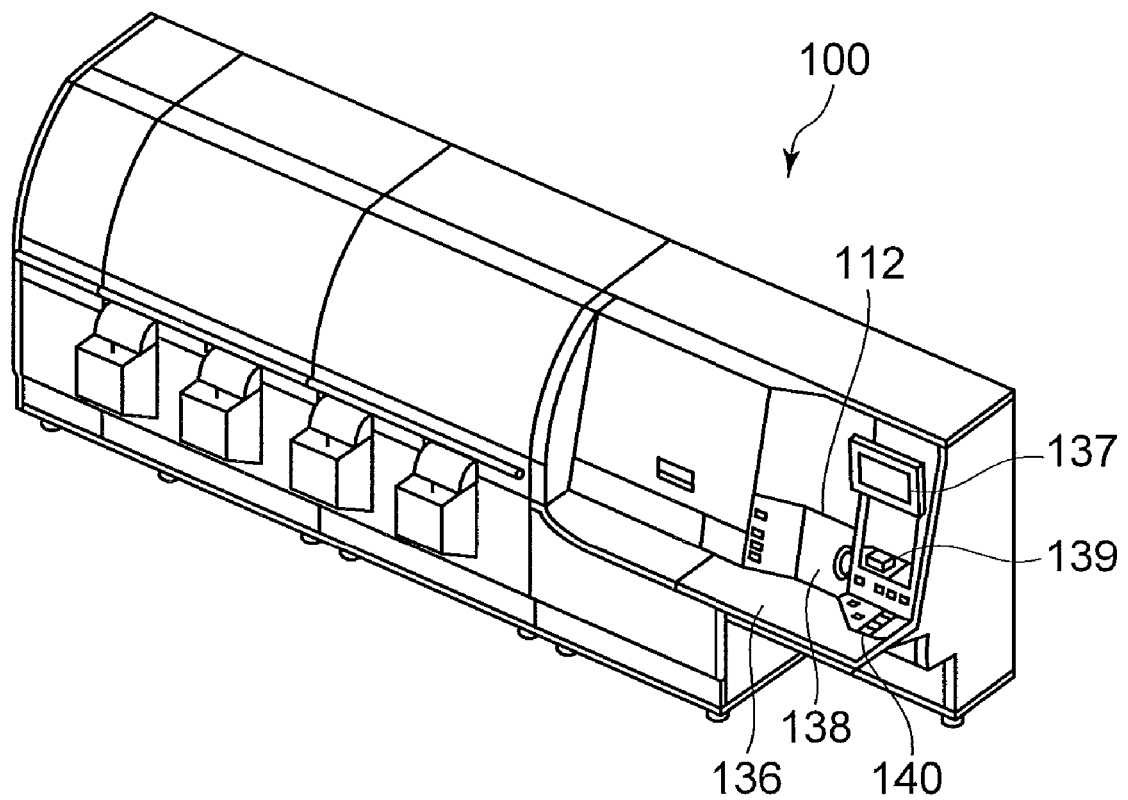
FIG. 15 is a perspective view showing the appearance of a paper handling apparatus according to one embodiment.

The following is an explanation of a paper handling apparatus including this limpness detecting device 10. FIG. 15 is a perspective view showing the appearance of a paper handling apparatus according to one embodiment. As shown in FIG. 15, the paper handling apparatus 100 includes, on the outside of the apparatus, an insert port 112, an operating portion 136, an operation/display portion 137, a door 138, a take-out port 139 and a keyboard 140.

The insert port 112 is configured so that sheets 7 can be inserted into it. The insert port 112 receives a batch of stacked sheets 7. The operating portion 136 receives various operation inputs from an operator. The operation/display portion 137 displays various kinds of operation guidance and processing results to the operator. It should be noted that the operation/display portion 137 may also be configured as a touch panel. In this case, the paper handling apparatus 100 senses various kinds of operation inputs based on buttons that are displayed on the operation/display portion 137, and the operation by the operator on the operation/display portion 137.

The door 138 is for opening and closing the insert opening of the insert port 112. A take-out port 139 is configured to retrieve the sheets 7 from a collection portion where the sheets 7 that have been judged by the sheet handling apparatus 100 to be unfit for recirculation are stacked. The keyboard 140 functions as an input section that receives various kinds of operation input from the operator.

Figure 16:
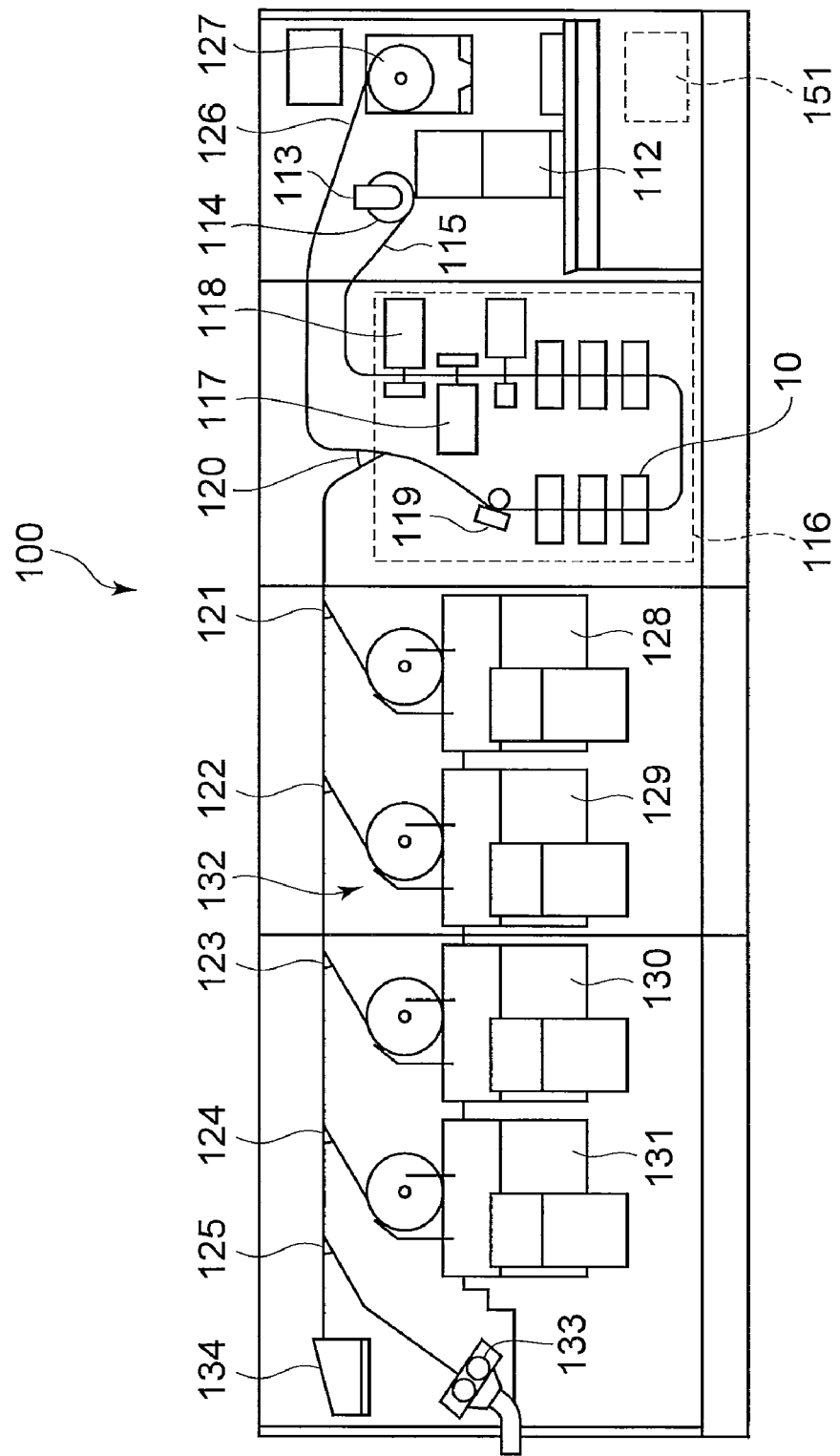
FIG. 16 is a diagrammatic view showing the configuration of the sheet handling apparatus shown in FIG. 15.

FIG. 16 is a diagrammatic view showing a configuration example of the sheet handling apparatus 100 shown in FIG. 15. The sheet handling apparatus 100 includes, on the inside of the apparatus, the insert port 112, the take-out port 113, a suction roller 114, a conveying route 115, an inspection portion 116, gates 120 to 125, a rejection sheet conveying route 126, a rejection sheet stacker 127, stack/band portions 128 to 131, a cutting portion 133, and a stacker 134. Moreover, the sheet handling apparatus 100 includes a main controller 151. The main controller 151 performs the integrated control of the operation of the various parts of the sheet handling apparatus 100.

The take-out port 113 is arranged above the insert port. The take-out port 113 includes the suction roller 114. The suction roller 114 is provided such that it contacts the sheets 7 placed into the insert port 112 at the upper end in stacking direction. That is to say, by rotating, the suction roller 114 takes in the sheets 7 placed in the insert port 112 one by one from the upper end in stacking direction into the apparatus. The suction roller 114 functions so as to take out one sheet 7 per rotation, for example. Thus, the suction roller 114 takes out the sheets 7 at constant pitch. The sheets 7 taken out by the suction roller 114 are introduced to the conveying route 115.

The conveying route 115 is a conveying unit for conveying the sheets 7 to the various parts inside the sheet handling apparatus 100. The conveying route 115 is provided with the conveying belts 5 and drive pulleys that are not shown in the drawings. The conveying route 115 causes the conveying belts 5 to operate with a drive motor and drive pulleys not shown in the drawings. The conveying route 115 conveys the sheet 7 taken out by the suction roller 114 at a constant speed with the conveying belts 5. It should be noted that in the following explanations, the side of the conveying route 115 closer to the take-out port 113, is regarded as the "upstream side", and the side of the conveying route 115 closer to the stacker 134 is regarded as the "downstream side".

The inspection portion 116 is provided on the conveying route 115 extending from the take-out port 113. The inspection portion 116 includes an image reader 117, an image reader 118, the limpness detecting device 10, and a thickness inspection portion 119. The inspection portion 116 detects optical feature information, mechanical features, and magnetic feature information of the sheets 7. Thus, the sheet handling apparatus 100 inspects the type, damage and dirt, front and back surface, and the genuineness of the sheets 7.

The image readers 117 and 118 are arranged on opposite sides flanking the conveying route 115. The image readers 117 and 118 read the images of both sides of the sheets 7 that are conveyed along the conveying route 115. The image readers 117 and 118 each include a charge-coupled device (CCD) camera. The sheet handling apparatus 100 obtains pattern images of the front surface and the back surface of the sheets 7, based on the images taken with the image readers 117 and 118.

The image readers 117 and 118 temporarily store the read images in a memory, which not shown in the drawings, inside the inspection portion 116. The sheet handling apparatus 100 displays the images stored in this memory on the operation/display portion 137, in accordance with the operation input.

As noted above, the limpness detecting device 10 detects the mechanical characteristics of the sheets 7. Thus, the limpness detecting device 10 judges whether the sheets 7 are worn out and damaged bills that are unfit for recirculation, or whether they are intact bills that are fit for recirculation.

The thickness inspection portion 119 inspects the thickness of the sheets 7 that are conveyed on the conveying route 115. For example, if the detected thickness has at least a predetermined value, the sheet handling apparatus 100 detects that two sheets 7 have been taken out at the same time.

Moreover, the inspection portion 116 includes a magnetic sensor that is not shown in the drawings. This magnetic sensor detects magnetic feature information concerning the sheets 7.

Based on the detection result from the image readers 117, 118, the limpness detecting device 10, the thickness inspection portion 119, and the magnetic sensor and the like, the main controller 151 judges whether the sheets 7 are intact bills, damaged bills or rejection bills.

The sheet handling apparatus 100 conveys the sheets 7 that have been judged to be intact bills to the stack/band portions 128 to 131. Moreover, the sheet handling apparatus 100 conveys the sheets 7 that have been judged to be damaged bills to a cutting portion 133. The cutting portion 133 cuts the conveyed damaged bills. It should be noted that the sheet handling apparatus 100 may also convey the damaged bills to the stacker 134 and stack them there. The stacker 134 applies a wrapper every time that for example 100 stacked damaged bills have arrived.

The rejection bills are sheets 7 that are neither intact bills nor damaged bills. The sheet handling apparatus 100 conveys the sheets 7 that have been judged to be rejection bills to the rejection sheet stacker 127. Rejection bills are for example improperly conveyed bills, such as double take-outs, defective bills, such as folded or ripped bills, and bills that could not be discriminated, such as wrong bill types or counterfeit bills.

The gates 120 to 125 are arranged in order along the conveying route 115 on the downstream side of the inspection portion 116. The gates 120 to 125 are each controlled by the main controller 151. The main controller 151 controls the operation of the gates 120 to 125 based on the inspection result from the inspection portion 116. Thus, the main controller 151 performs the control such that the sheets 7 conveyed on the conveying route 115 are conveyed to a predetermined processing portion.

The gate 120 arranged immediately behind the inspection portion 116 branches the conveying route 115 to a rejection sheet conveying route 126. That is to say, as a result of the inspection with the inspection portion 116, the gate 120 is switched such that the rejection bills that have been judged not to be legitimate bills, the bills that could not be inspected by the inspection portion 116 and the like are conveyed to the rejection sheet conveying route 126.

The rejection sheet stacker (rejection portion) 127 is provided at the rear end of the rejection sheet conveying route 126. The rejection sheet stacker 127 stacks the above-noted rejection bills, and bills that could not be inspected and so on mentioned above, in the orientation in which they were taken out from the take-out port 113. The sheets 7 stacked in the rejection sheet stacker 127 can be taken out from the take-out port 139.

Moreover, the stack/band portions 128 to 131 (collectively referred to as "stack and band portion 132") are provided respectively behind the branching of the gates 121 to 124. The sheets 7 that have been judged to be fit for recirculation are stacked in the stack and band portion 132, sorted by type and front/rear side. The stack and band portion 132 bands and stores the stacked sheets 7 in packs of a predetermined number. Moreover, every predetermined number of packs, the sheet handling apparatus 100 stacks and bands a plurality of packs of sheets 7 with a large-pack band portion, not shown in the drawings.

The cutting portion 133 is arranged behind the branching of the gate 125. The cutting portion 133 cuts and stores sheets 7. The sheets 7 that are conveyed by the gate 125 are legitimate sheets 7 that have been judged to be unfit for recirculation (damaged bills).

The stacker 134 is placed at the end of the other conveying route branched by the gate 125. If the damaged bill cutting mode is selected, the main controller 151 controls the gate 125 such that the sheets 7 are conveyed to the cutting portion 133. And if the damaged bill cutting mode is not selected, the main controller 151 controls the gate 125 such that the sheets 7 are conveyed to the stacker 134.

The main controller 151 successively stores the number of sheets 7 stacked by the stack and band portion 132, the number of sheets 7 cut by the cutting portion 133, and identification information.

Figure 17:
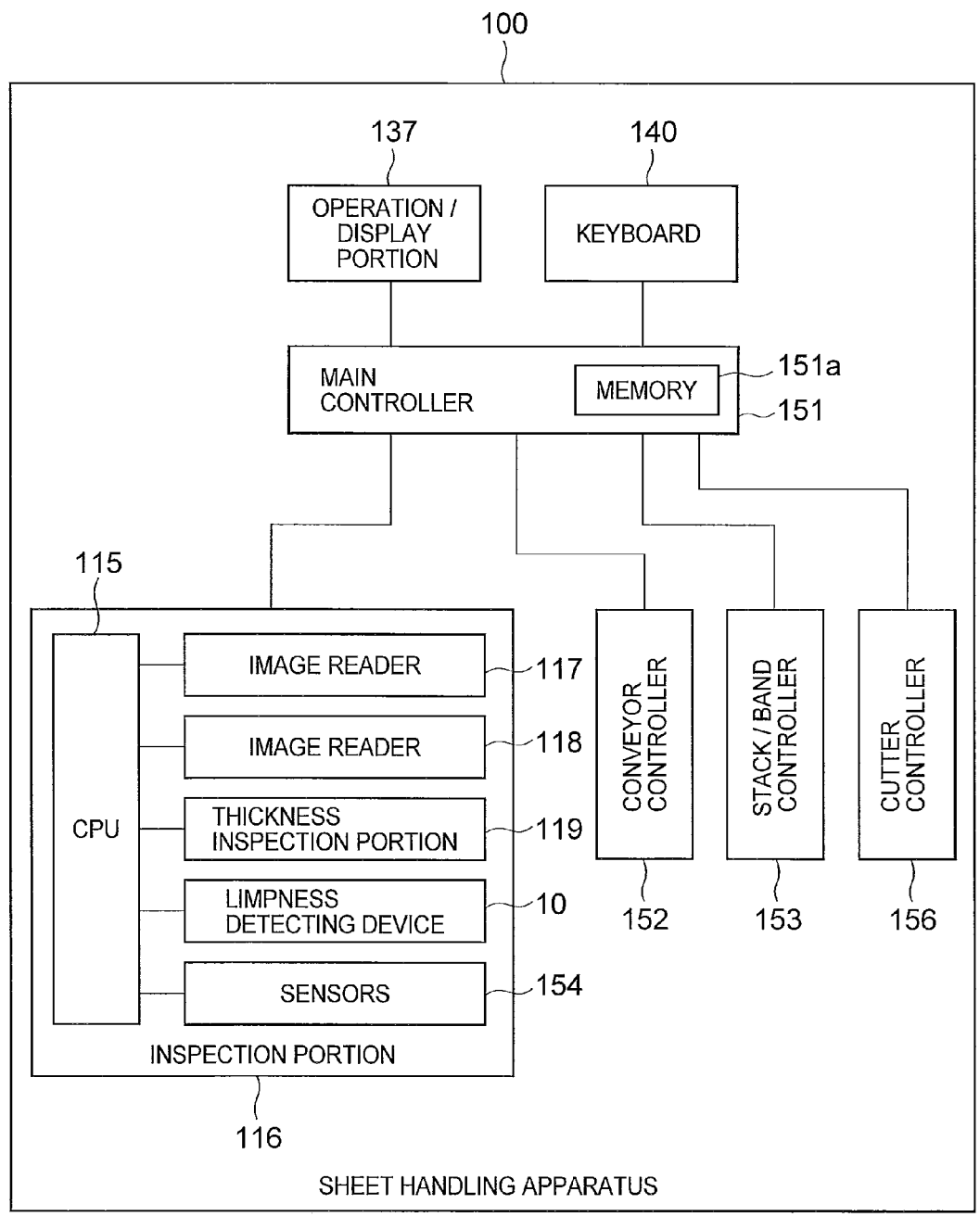
FIG. 17 is a block diagram showing the configuration of a control system of the sheet handling apparatus shown in FIG. 15 and FIG. 16.

FIG. 17 is a block diagram illustrating a configuration example of a control system of the sheet handling apparatus 100 shown in FIG. 15 and FIG. 16.

The sheet handling apparatus 100 includes the main controller 151, the inspection portion 116, the conveyor controller 152, the stack/band controller 153, the cutter controller 156, the operation/display portion 137, and the keyboard 140.

The main controller 151 performs the overall control of the sheet handling apparatus 100. The main controller 151 controls the conveyor controller 152 and the stack/band controller 153 based on the commands entered into the operation/display portion 137 and the inspection result from the inspection portion 116.

For example, an operator enters the bill type and number, the intactness discrimination level, the name of the supplier and the processing method of the processed sheets 7 with the operation/display portion 137 or the keyboard 140.

The inspection portion 116 includes the image readers 117 and 118, the thickness inspection portion 119, the limpness detecting device 10, other sensors 154 and a CPU 155.

The image readers 117 and 118 read an image from both sides of the sheets 7 that are conveyed on the conveying route 115. The image readers 117 and 118 include a light-receiving element, such as a CCD, and an optical system. The image readers 117 and 118 project light onto the conveyed sheets 7 and receive the reflected light or the transmitted light with the optical system. The image readers 117 and 118 image the light received with the optical system onto the CCD and obtain an electric signal (image).

The main controller 151 stores an image (reference image) serving as a reference for the sheet 7 in advance in a memory 151a. The main controller 151 subjects the sheets to an intactness judgment and a counterfeit bill judgment by comparing the image obtained from the sheets 7 with the reference image stored in the memory 151a.

As described above, the limpness detecting device 10 irradiates acoustic waves with the transmitter 1 onto the conveyed sheets 7. The limpness detecting device 10 receives, with the receivers 2A and 2B, leaky waves of the Lamb waves leaking from the front surface and the back surface of the sheets 7. The controller 9 of the limpness detecting device 10 calculates the average value 91, based on the signal detected with the receivers 2A and 2B.

The controller 9 compares the standard value stored in the standard value memory 15 with the calculated average value 91, and judges whether the sheets 7 are intact bills. Thus, the limpness detecting device 10 can judge whether the sheets 7 are fit for recirculation as intact bills.

The thickness inspection portion 119 inspects the thickness of the sheets 7 that are conveyed on the conveying route 115. The other sensors 154 are for example magnetic sensors or the like. The magnetic sensors detect information on magnetic features from the sheets 7 that are conveyed on the conveying route 115.

Based on the result of the inspection with the image readers 117 and 118, the thickness inspection portion 119, the limpness detecting device 10, and the other sensors 154, the CPU 155 discriminates the type, the intactness, the front and back surface and the genuineness of the sheets 7 that are conveyed on the conveying route 115.

Based on the control of the main controller 151, the conveyor controller 152 controls the take-out port 113, the conveying route 115, the rejection sheet conveying route 126, and the gates 120 to 125. Accordingly, the conveyor controller 152 controls the take-out and the conveying of the sheets 7. Moreover, the conveyor controller 152 performs a sorting process, in which the judged sheets 7 are sorted by type. That is to say, the conveyor controller 152 functions as a sorting processor. It should be noted that the conveyor controller 152 sorts the sheets 7 by type, but there is no limitation to this. For example, it may also process the sheets 7 by sorting them according to their degree of bill fatigue, based on the detection result of the limpness detecting device 10.

The stack/band controller 153 controls the rejection sheet stacker 127 and the stack/band portions 128 to 131 based on the control of the main controller 151. Thus, the stack/band controller 153 controls the stacking and the banding of the sheets 7.

The cutter controller 156 controls the operation of the cutting portion 133 based on the control of the main controller 151. Thus, the cutting portion 133 performs the cutting of the conveyed sheets 7.

As explained above, the sheet handling apparatus 100 including the limpness detecting device 10 according to an embodiment of the present invention inspects the sheets 7 with the limpness detecting device 10. The limpness detecting device 10 inspects the mechanical characteristics of the sheets 7 and judges whether the sheets 7 are fit for recirculation. The sheet handling apparatus 100 can process the sheets 7 as appropriate, based on the result of that judgment.

While certain embodiments have been described, those embodiments have been presented by way of example only, and are not intended to limit the scope of the inventions. Indeed, the novel methods and apparatuses described herein may be embodied in a variety of other forms; furthermore, various omissions, substitutions and changes in the form of the methods and apparatuses described herein may be made without departing from the spirit of the inventions. The accompanying claims and their equivalents are intended to cover such forms or modifications as would fall within the scope and spirit of the inventions.

What is claimed is:

1. A limpness detecting device comprising:
    a transmitting unit to irradiate an acoustic wave towards a conveyed bill to excite a Lamb wave;
    a first receiving unit to detect a leaky wave of the Lamb wave leaked from a front surface of the bill as an amplitude of the wave;
    a second receiving unit to detect a leaky wave of the Lamb wave emitted from a back surface of the sheet;
    a comparison data calculating unit to calculate comparison data based on the amplitude of the wave detected by the first receiving unit and the amplitude of the wave detected by the second receiving unit; and
    an intactness judgment unit to compare the comparison data calculated by the comparison data calculating unit with a preset standard value and to judge whether the bill is an intact bill or not, based on a result of the comparison.

2. The device according to claim 1, wherein the first receiving unit and the second receiving unit are placed at positions of detection by the first receiving unit and the second receiving unit that are each spaced apart from the transmitting unit by the same distance.

3. The device according to claim 1, wherein the comparison data calculated by the comparison data calculating unit is an average value of the amplitude of the wave detected by the first receiving unit and the amplitude of the wave detected by the first receiving unit.

4. The device according to claim 1, further comprising:
    a first gain regulator unit to regulate gain of the amplitude of the wave detected by the first receiving unit; and
    a second gain regulator unit to regulate gain of the amplitude of the wave detected by the second receiving unit;
    wherein the comparison data calculated by the comparison data calculating unit is an average value of the amplitude of the wave that is gain-regulated by the first gain regulator unit and the amplitude of the wave that is gain-regulated by the second gain regulator unit.

5. The device according to claim 1, wherein the intactness judgment unit compares the comparison data calculated by the comparison data calculating unit with a preset standard value, and judges that the bill is a damaged bill if the comparison data calculated by the comparison data calculating unit is not greater than the preset standard value.

6. The device according to claim 1, wherein the first receiving unit and the second receiving unit detect a leaky wave from an entire conveyance region through which the bill is conveyed.

7. The device according to claim 6, wherein the first receiving unit and the second receiving unit comprise a plurality of receiving sensors that are lined up in a direction at a right angle with a conveying direction of the bill.

8. The device according to claim 6, wherein the first receiving unit and the second receiving unit comprise a receiving sensor having a length, in a direction at a right angle with a conveying direction of the bill, of at least the conveyance region through which the bill is conveyed.

9. The device according to claim 1, further comprising:
    a third receiving unit to detect a percolation wave that is transmitted from the transmitting unit and percolates through the bill, the third receiving unit being arranged opposite the transmitting unit on the other side of the bill; and
    a sensing unit that senses overlapping of bill and/or foreign matter adhering to the sheet, based on the amplitude of the wave detected by the third receiving unit.

10. The device according to claim 1, further comprising:
    a third receiving unit to detect a percolation wave that is transmitted from the transmitting unit and percolates through the bill, the third receiving unit being arranged opposite the transmitting unit on the other side of the sheet;
    wherein the intactness judgment unit judges a fatigue of the bill, based on the amplitude of the wave detected by the third receiving unit and the comparison data calculated by the comparison data calculating unit, and judges whether the bill is intact, based on the judged fatigue.

11. A limpness detecting method comprising:
    exciting a Lamb wave by irradiating an acoustic wave towards a conveyed bill;
    detecting a leaky wave of the Lamb wave emitted from a front surface of the bill;
    detecting a leaky wave of the Lamb wave emitted from a back surface of the bill as an amplitude of the wave;

calculating comparison data based on the signal detected from the front surface of the bill and the amplitude of the wave detected from the back surface of the bill; and comparing the calculated comparison data with a preset standard value and judging whether the bill is an intact bill or not, based on a result of the comparison.

12. A bill handling apparatus comprising:

a conveying portion to convey the bill;

the limpness detecting device according to claim 1 configured to judge whether the bill is an intact bill or not; and a sorting processor to sort the bill based on a result of the judgment by the intactness judgment unit.

13. The apparatus according to claim 12, wherein:

the limpness detecting device further comprising;

a first gain regulator unit to regulate gain of the amplitude of the wave detected by the first receiving unit; and a second gain regulator unit to regulate gain of the amplitude of the wave detected by the second receiving unit;

wherein the comparison data calculated by the comparison data calculating unit is an average value of the amplitude of the wave that is gain-regulated by the first gain regulator unit and the amplitude of the wave that is gain-regulated by the second gain regulator unit.

14. The apparatus according to claim 12, wherein:

the limpness detecting device further comprising;

a third receiving unit to detect a percolation wave that is transmitted from the transmitting unit and percolates through the bill, the third receiving unit being arranged opposite the transmitting unit on the other side of the bill; and a sensing unit that senses overlapping of bills and/or foreign matter adhering to the bill, based on the amplitude of the wave detected by the third receiving unit.

* * * * *